United States Patent [19]

Stoop

[11] Patent Number: 5,549,648
[45] Date of Patent: Aug. 27, 1996

[54] PACEMAKER SYSTEM AND METHOD WITH IMPROVED DETECTION OF END OF RETROGRADE CONDUCTION

[75] Inventor: Gustaaf A. P. Stoop, Dieren, Netherlands

[73] Assignee: Vitatron Medical, B.V., Dieren, Netherlands

[21] Appl. No.: 412,963

[22] Filed: Mar. 29, 1995

[51] Int. Cl.$^6$ .................................................. A61N 1/362
[52] U.S. Cl. .................................................. 607/9
[58] Field of Search ............................ 607/9, 14, 27

[56] References Cited

U.S. PATENT DOCUMENTS

| | | |
|---|---|---|
| 4,452,248 | 6/1984 | Keller, Jr. . |
| 4,467,807 | 8/1984 | Bornzin . |
| 4,515,161 | 5/1985 | Wittkampf et al. . |
| 4,527,568 | 7/1985 | Rickards . |
| 4,539,991 | 9/1985 | Boute et al. . |
| 4,543,963 | 10/1985 | Gessman . |
| 4,554,920 | 11/1985 | Baker, Jr. et al. . |
| 4,554,921 | 11/1985 | Boute et al. . |
| 4,686,989 | 8/1987 | Smyth et al. . |
| 4,917,115 | 4/1990 | Flammang et al. . |
| 4,920,965 | 5/1990 | Funke et al. . |
| 4,951,667 | 8/1990 | Markowitz . |
| 5,065,759 | 11/1991 | Begemann et al. . |
| 5,193,550 | 3/1993 | Duffin . |
| 5,228,438 | 7/1993 | Buchanan . |
| 5,231,985 | 8/1993 | Sutton et al. .............. 607/18 |
| 5,247,929 | 9/1993 | Stoop et al. ............... 607/14 |
| 5,253,644 | 10/1993 | Elmvist ....................... 607/14 |
| 5,312,450 | 5/1994 | Markowitz .................. 607/14 |

*Primary Examiner*—William E. Kamm
*Assistant Examiner*—Scott M. Getzow
*Attorney, Agent, or Firm*—Woodcock Washburn Kurtz Mackiewicz & Norris

[57] ABSTRACT

A dual chamber pacemaker system and method are provided for placing the pacemaker in an asynchronous mode when retrograde conduction is present, having the capability of detecting the onset of retrograde conduction and also monitoring on a cycle-by-cycle basis to determine the end of retrograde conduction. The detection of end of retrograde conduction is accomplished by two operative algorithms, i.e., a first algorithm which is executed at the time of any atrial sense and a second algorithm which is executed at the time of each ventricular event. Following an atrial sense, the pacemaker checks to see whether the just concluded VA interval conforms to predetermined RC interval criteria, and if not, immediately switches the pacemaker out of the RC mode and into a synchronous tracking mode. Following each ventricular event while the pacemaker is in the RC mode, the pacemaker monitors a predetermined class of special events and determines end of RC upon detection of a pattern of such special events. In a specific embodiment, if there are n (e.g.,3) consecutive cycles wherein the VA interval differs from the VA interval of the previous cycle by more than a predetermined amount, this is determined to establish a pattern indicative of end of RC; upon detection of this pattern, the pacemaker immediately switches to a synchronous tracking mode of pacing.

15 Claims, 5 Drawing Sheets

PACEMAKER SYSTEM AND METHOD WITH IMPROVED DETECTION OF END OF RETROGRADE CONDUCTION

BACKGROUND OF THE INVENTION

1. Field Of the Invention

This invention relates to cardiac pacing systems and, more particularly, to dual chamber pacing systems designed to react to an occurrence of retrograde conduction by switching to a different mode of operation; to detect when such retrograde conduction has ended; and to resume normal synchronous tracking directly upon detected end of retrograde conduction.

2. Description of the Prior Art

The advantages of dual chamber pacing, and more particularly pacing in different modes which are selected in response to different patient conditions, is now well recognized in the art. Early pacing systems were solely ventricular, and were sufficient for management of patients with complete heart block and Stokes-Adams attacks. However, ventricular demand pacemakers are not equipped to take advantage of atrial activity, and thus are limited in their efficiency. Subsequently, atrial synchronous, ventricular pacemakers were introduced, having a lead for sensing P signals from the atrium and another for pacing the ventricle after a suitable P-R (A-V) interval. Such a pacemaker, e.g. VDI or VDD, allows the atrium to control the heart's response rate, the ventricle being paced at the atrial rate up to a predetermined upper rate limit. Such synchronous pacers have incorporated means for dealing with high atrial rates, including "block" and "Wenckebach" technic ues.

Another form of A-V or dual chamber pacer that has been utilized is the sequential pacemaker (DVI), which paces both the atrium and the ventricle with an appropriate A-V delay which is timed by the pacemaker. A number of commercial pacemakers have been introduced which are programmable to these and other known pacing modes. Each of the various operating modes is particularly adapted to certain circumstances that may arise in a given patient.

Since the dual sense-dual pace DDD pacemaker became commercially available, it has gained favor for the reason that it compensates for many of the disadvantages of other pacemaker modes. The classic DDD pacemaker is described in U.S. Pat. No. 4,920,965, Funke et at., in some detail. See also U.S. Pat. Nos. 4,539,991 and 4,554,921, incorporated herein by reference, which disclose other forms of DDD-type pacemakers.

More recently, the DDDR pacemaker has come to prominence. In this type of pacemaker, there is provided one or more sensors which enable the pacemaker to be rate responsive, such that the pacing interval, or escape interval, is varied as a function of one or more sensed rate-indicating parameters, rather than being fixed at a programmed value. In the DDDR pacemaker, both atrial and ventricular natural beats may occur so long as they occur prior to the respective rate responsive escape interval. See U.S. Pat. Nos. 4,467,807 and 4,951,667, which are illustrative of dual chamber rate responsive pacemakers.

There have also been disclosed multi-mode pacemaker designs having means for switching modes in response to changing patient conditions. Most dual chamber pacemakers are programmable to distinct modes, or switch automatically from one mode to another under certain prescribed conditions. See, for example, U.S. Pat. Nos. 4,527,568, and 4,920,965. However, there remains a substantial need in the pacing art for sensing the conditions under which a dual chamber pacemaker can or should be controlled to change mode, and for providing optimum flexibility for blending two or more modes of operation. Thus, instead of forcing the pacer to operate in a distinct mode until patient history enables switching to another distinct mode, the pacer is optimally enabled to react on a cycle-to-cycle basis to sensed events. For example, while it is desirable to synchronize a delivered ventricular stimulus to a sensed atrial signal whenever possible, at the same time the pacemaker should be controlled to adopt another more optimum response whenever desired. Thus, if an atrial sensed beat occurs at too high a rate, or if retrograde conduction is determined, the pacemaker should have the flexibility to respond quickly and appropriately to the situation.

It is known in the pacemaker art to provide for control of pacemaker-mediated tachycardia (PMT). See U.S. Pat. No. 5,247,929, assigned to the same assignee as this invention, and incorporated herein by reference. In the pacemaker of the referenced patent, when retrograde conduction (RC) is detected, the pacemaker switches from a synchronous tracking mode into an asynchronous mode, i.e., ventricular pace pulses are delivered without regard to the timing of the atrial signals. Of course, when the pacemaker goes into such an asynchronous mode of operation, it becomes important to sense when the retrograde conduction is ended, so that the pacemaker can go back to normal synchronous tracking operation. In the pacemaker of the referenced patent, the system waits until either the occurrence of certain patterns of events that indicate the end of RC, or until the expiration of a programmed wait time following which the pacemaker goes through a routine for checking to determine the presence of RC. This routine involves an active search carried out by changing the AV or VV interval to a different, predetermined interval for a number of consecutive cycles, and monitoring of the resulting VA interval. A measure of the resulting VA interval is determined and analyzed for VA equality, i.e., substantially equal VA intervals indicate an RC condition. If such equality is not determined, the pacemaker can conclude that RC has ended. However, this procedure is subject to situations where RC had ended before the search was initiated. Alternately, the search can be conducted too early, resulting in recurrent PMTs for some duration of operation.

In view of the prior art, there remains a substantial need for a dual chamber pacing system which optimally reacts to episodes of RC by switching into an asynchronous mode of operation, and then quickly returns to synchronous tracking of atrial signals when the RC has ended. The specific need is for a system of detecting end of RC as quickly has can be reliably done, even on a cycle-by-cycle basis when appropriate.

SUMMARY OF THE INVENTION

It is a primary object of this invention to provide a dual chamber system and method having the capability of determining when retrograde conduction has commenced and also when it has ended, and specifically for determining quickly when retrograde conduction has ended and thereupon taking the pacemaker out of the RC mode and returning it to normal synchronous tracking.

In accordance with the above object, there is provided a dual chamber pacemaker for normally providing ventricular pace pulses in synchronized relation to the patient's atrial events, and having the capability of determining the occurrence of retrograde conduction and placing the pacemaker in an RC mode of asynchronous operation when such RC conduction is determined. The pacemaker is further characterized by the feature of determining when the retrograde conduction has stopped, or ended (RC_End). The detection of RC_End is accomplished in two parts, namely by a first algorithm which is executed at the time of each atrial sense, and a second algorithm which is executed at the time of each ventricular event. Following an atrial sense, the pacemaker checks the VA interval with respect to RC interval criteria, e.g., whether the VA interval is within an RC range of about 150–450 ms. If the interval is outside of these limits, it is deemed to be not RC, and the RC mode is ended immediately. Also, if a second atrial sense is detected in the current V-V interval, this is also acted upon as detection of end of RC. Following a ventricular event, the pacemaker routine ends RC directly if there has been an atrial sync pulse, or if there have been three successive cycles having any one of a predetermined class of special event. In particular, if the VA interval compared to the previous VA interval indicates a certain level of change, or instability, this is deemed to be such a special event, and three successive cycles having such VA instability result in a determination of end of RC.

DESCRIPTION OF THE PREFERRED EMBODIMENTS

Figure 1:
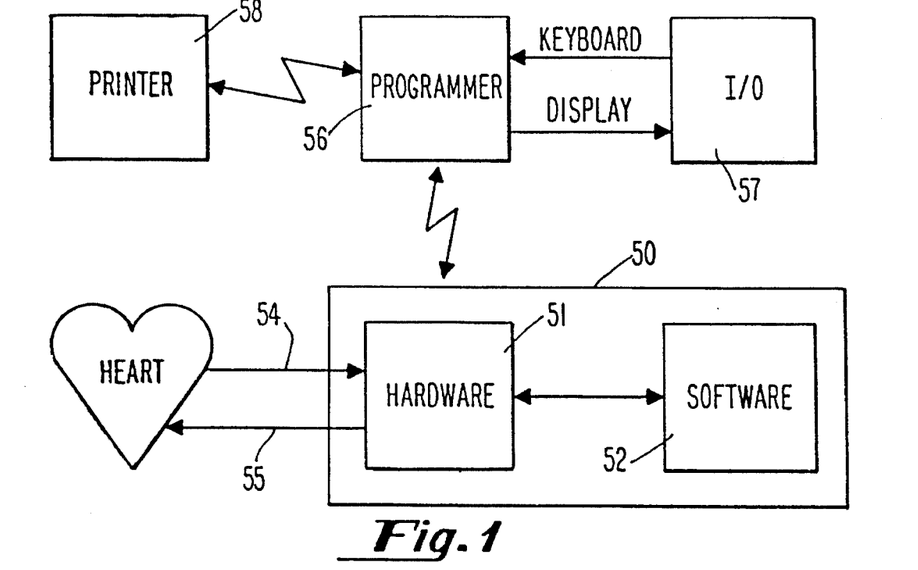
FIG. 1 is a block diagram of the overall system of the invention, showing the environment in which the pacemaker operates.

The pacing system of this invention is preferably software-based, i.e., the software controls functions through hardware, as illustrated in FIG. 1. Referring specifically to FIG. 1, the pacemaker 50 is shown as having a component hardware portion 51 and a software portion 52, the two portions being interconnected. The software is parameter-driven, i.e., there are numerous parameters that control the pacing behavior, diagnostic functions, etc. The hardware is interconnected with the patient's heart by one or more electrodes on lead 55, and one or more sensor connections 54. As is well understood in the art, for a dual chamber pacemaker, there are generally two leads, an atrial lead and a ventricular lead, each lead having at least one electrode, unipole or bipole, positioned in the heart. For a VDD pacing system, there is only one lead, but there are still separate A and V electrodes. Line 54 is illustrated as leading to the heart, as in a QT-type sensor arrangement, but may be attached to the outside case of the pacemaker or may couple to any other available sensors for sensing body parameter information used in rate responsive pacing systems. Further, in the preferred embodiment of the pacing system of this invention, sensor link 54 may comprise a pair of sensors, e.g., QT plus activity, as set forth in U.S. Pat. No. 5,065,759.

As further illustrated in FIG. 1, the pacer 50 is in telemetric communication with a programmer 56. The user can select parameters and program them through programmer 56, and can also interrogate parameter and diagnostic data from the implanted pacemaker. Interrogated information from the pacer can be coupled by telemetry directly to a printer 58. Input/output devices 57 are used to input information by the user to the programmer, or to display information received by the programmer from the pacemaker.

Figure 2:
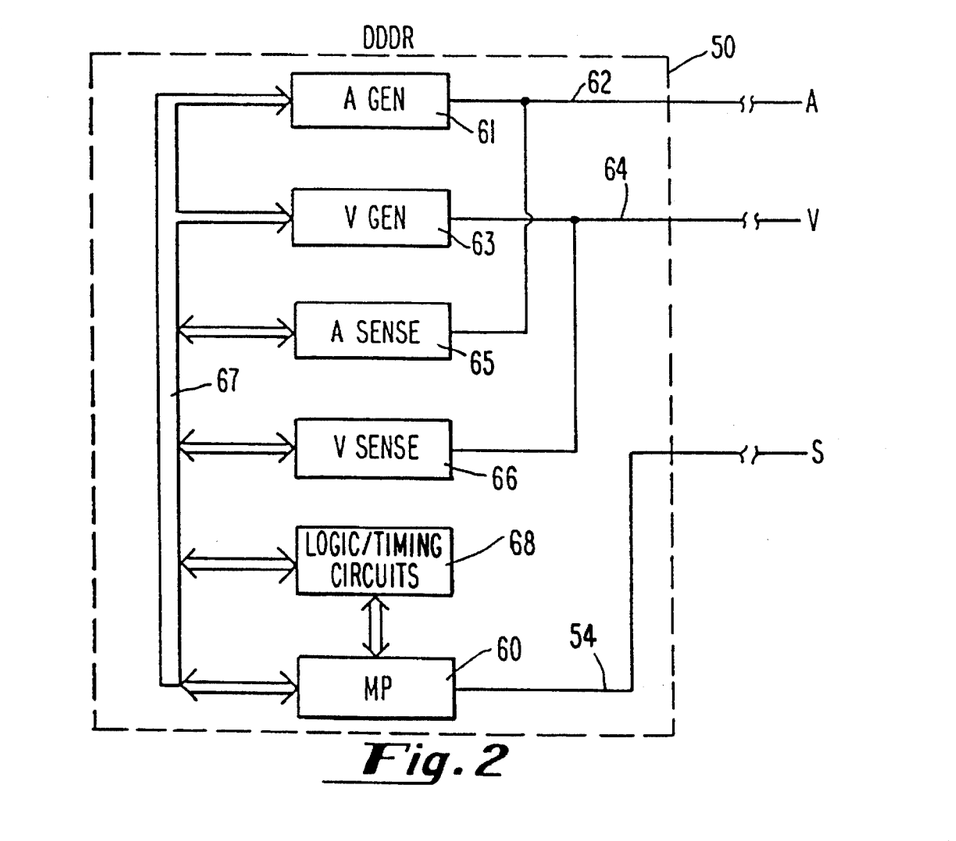
FIG. 2 is a block diagram which illustrates basic components of the pacemaker of this invention, together with leads and a sensor for delivering signals to and/or receiving signals from the patient.

Referring to FIG. 2, there is shown a basic block diagram of primary hardware components of a DDDR pacer 50. An atrial generator 61 is shown, having an output connected to lead 62 which communicates with the patient's atrium. An A-sense amplifier 65 is illustrated also connected to atrial lead 62. A ventricular generator is illustrated which is connected to the patient's ventricle through lead 64. V-sense amplifier 66 is also connected to lead 64, to receive and sense signals from the patient's ventricle. In one embodiment of this invention which preferably incorporates QT rate control, V-sense block 66 also includes means for picking out and determining the timing of the evoked T wave. Generators 61 and 63 and sense blocks 65 and 66 are interconnected with microprocessor system 60, which microprocessor has software which is parameter-driven to control the operation of the hardware units. Microprocessor system 60 may be interconnected with hardware logic and/or timing circuits 68. As affects the scope of this invention, the degree to which software supplants hardware, or vice versa, is a matter of design choice. Thus, for the many timing functions that are carried out in the pacing system of this invention, it is to be understood that the microprocessor may have built in timing circuits, or suitably may control external hardware timer circuits. Software control of pacing function is well known in the art, such that the following detailed discussions of software routines enable one of ordinary skill in this art area to design a system for carrying out the functions within the scope of the invention. Data inputted from programmer 56 is stored in memory associated with microprocessor.

Still referring to FIG. 2, there is shown a sensor S indicated as providing an input to microprocessor system 60. Sensor S represents one or more sensors for monitoring one or more body parameters to provide an indication of desired pacing rate. The pacemaker of this invention may be rate responsive in the manner as described in the referenced U.S. Pat. No. 5,247,929.

Figure 3A:
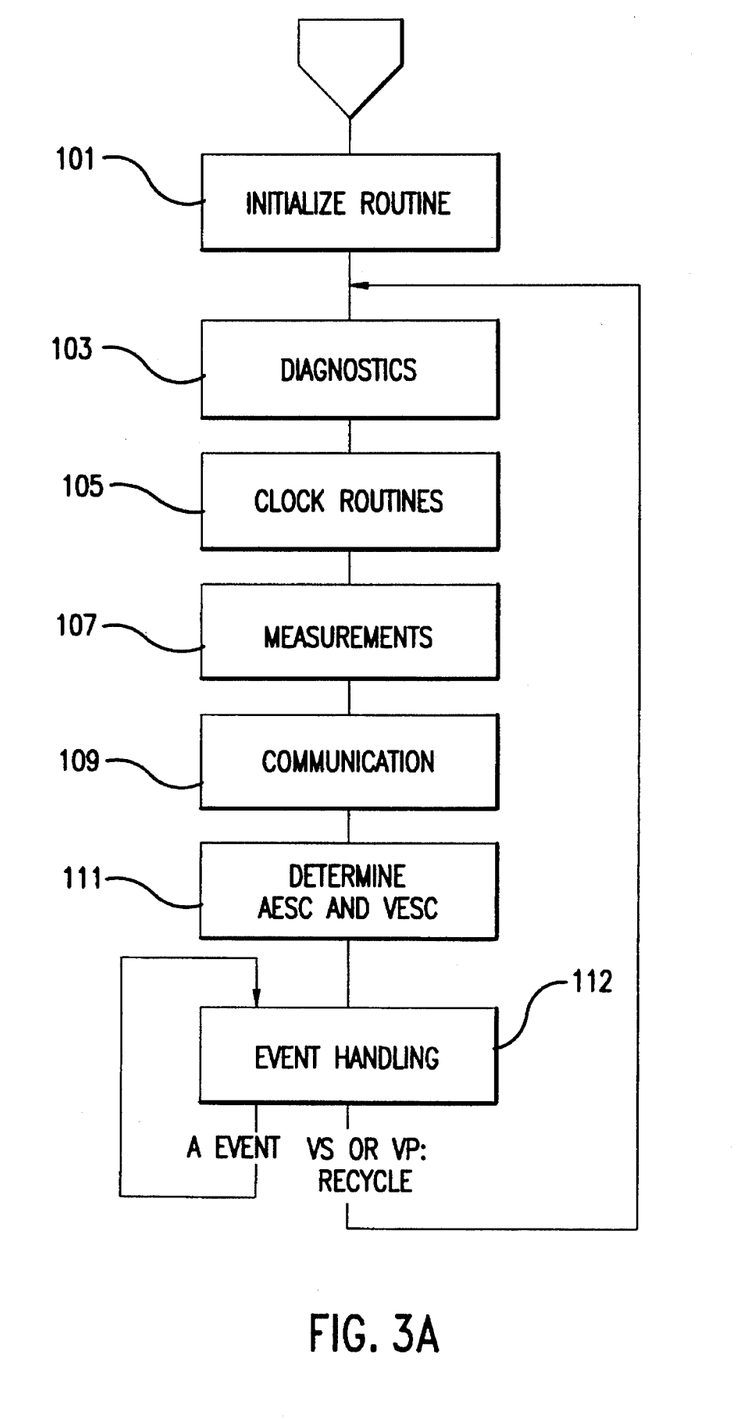
FIG. 3A is a flow diagram of the primary operations and overall logic structure of the pacemaker of this invention, showing the main sequential steps carded out each cycle.

Referring now to FIG. 3A, there is shown an illustrative flow diagram of basic logical steps taken by the pacemaker of this invention. The basic rules of operation are as follows:

For DDD(R) mode, V_esc=f(sensor, sinus), and

A_esc=V_esc—AV delay;

For VDD(R) mode, V_esc=f(sensor, sinus), and

A_esc is not started.

Note also that the two escape intervals may be varied for other purposes, such as hysteresis.

The routine is initialized at 101. Following this, any diagnostics built into the pacer are performed at block 103;

clock routines are done at block 105; measurements are performed and measure data stored at 107; and any communications with an external device, such as programmer 56, are done at step 109. The routine then goes to step 111, and determines A__esc and V__esc for the coming cycle. Of course, for a VDD pacer, no A__esc is determined. When the pacemaker is operating in a synchronous tracking mode, V__esc is reset to time out the AV delay from the time of the atrial sense; when operating in an asynchronous mode, as results from a determination of retrograde conduction, V__esc is not affected tied to the atrial sense. Following this, the pacemaker carries out event handling at 112, i.e., it reacts to atrial and/or ventricular senses, and delivers pace pulses as required by timeout of escape intervals. Following the ventricular event, either VS or VP, the pacer returns for the next cycle.

Figure 3B:
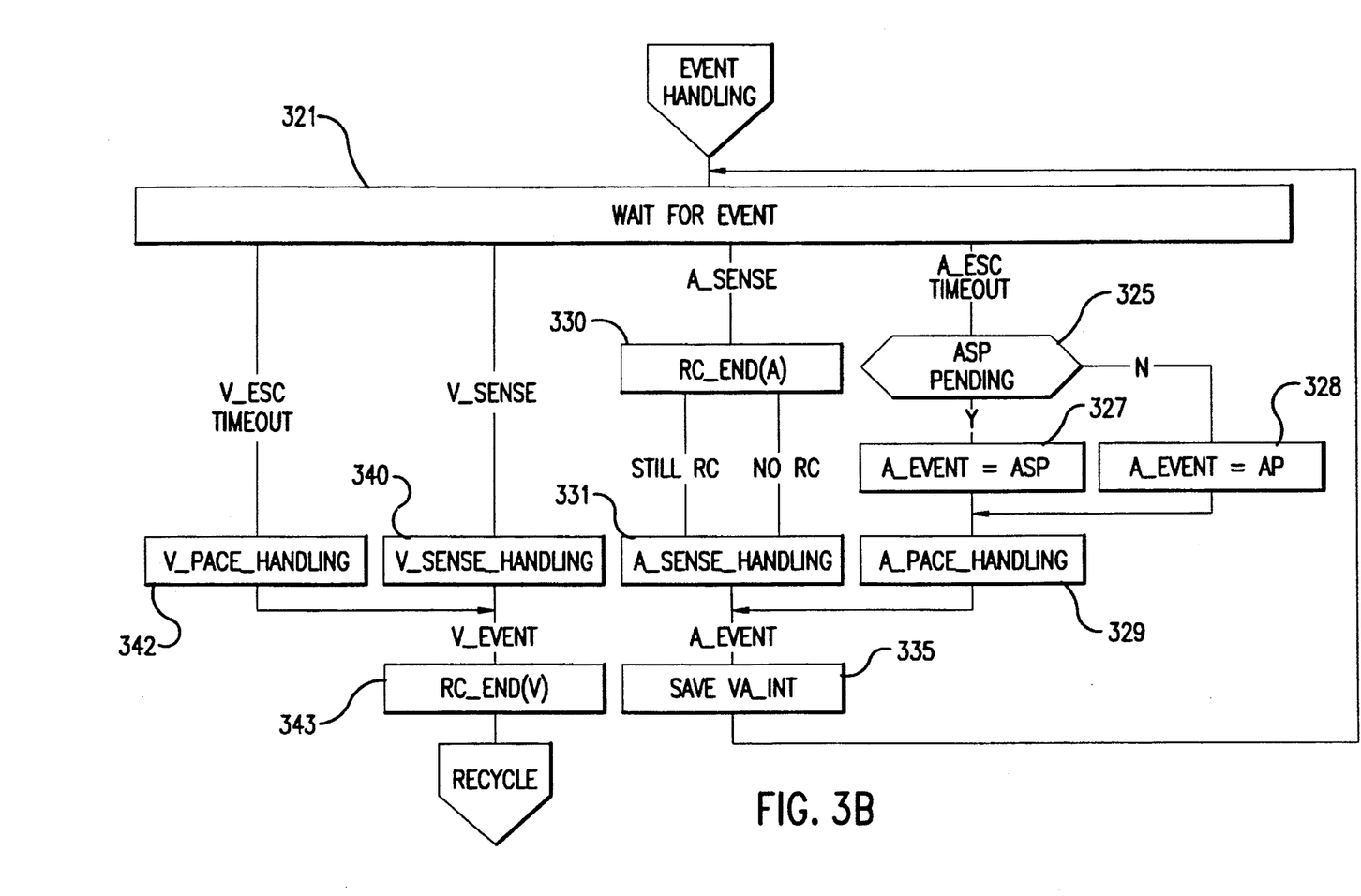
FIG. 3B is a flow diagram of basic sense and pace handling, i.e., how the pacemaker responds to an atrial sense (AS) or ventricular sense (VS); and when it delivers an atrial pace pulse (AP), atrial sync pulse (ASP) or ventricular pace pulse (VP).

Referring now to FIG. 3B, there is shown a more detailed flow diagram of the sense and pace handling. The routine is entered when no A event has yet occurred during the cycle. At block 321, the pacemaker waits for an event. As indicated, there are four possibilities (handling a T-sense, as in a Q-T pacemaker, is not described). Proceeding from right to left, there can be a timeout of the atrial escape interval, A_Esc, in which case the pacemaker goes to block 325 and determines whether an atrial sync pulse (ASP) is pending. If yes, at 327 the atrial event is stored as an ASP. If no, at block 328 the pacemaker records the event as an AP. The pacemaker then goes to block 329 for A_Pace handling, i.e., delivery of a suitable atrial pace pulse. Returning to block 321, if there is an A-sense, the pacemaker goes to block 330 and carries out the RC_End(A) routine, to determine whether RC has ended. The RC_End(A) routine concludes by indicating either "still RC" or "No RC". The pacemaker then proceeds with A-sense handling at block 331, e.g., following through with an appropriate response such as synchronous or asynchronous operation. See U.S. application Ser. No. 08/329,232, filed Oct. 26, 1994, and incorporated herein by reference. After A_Sense or A_Pace_ Handling, at 335 the pacemaker determines and saves VA__int, which is measured from a V event to an A event.

Figure 5:
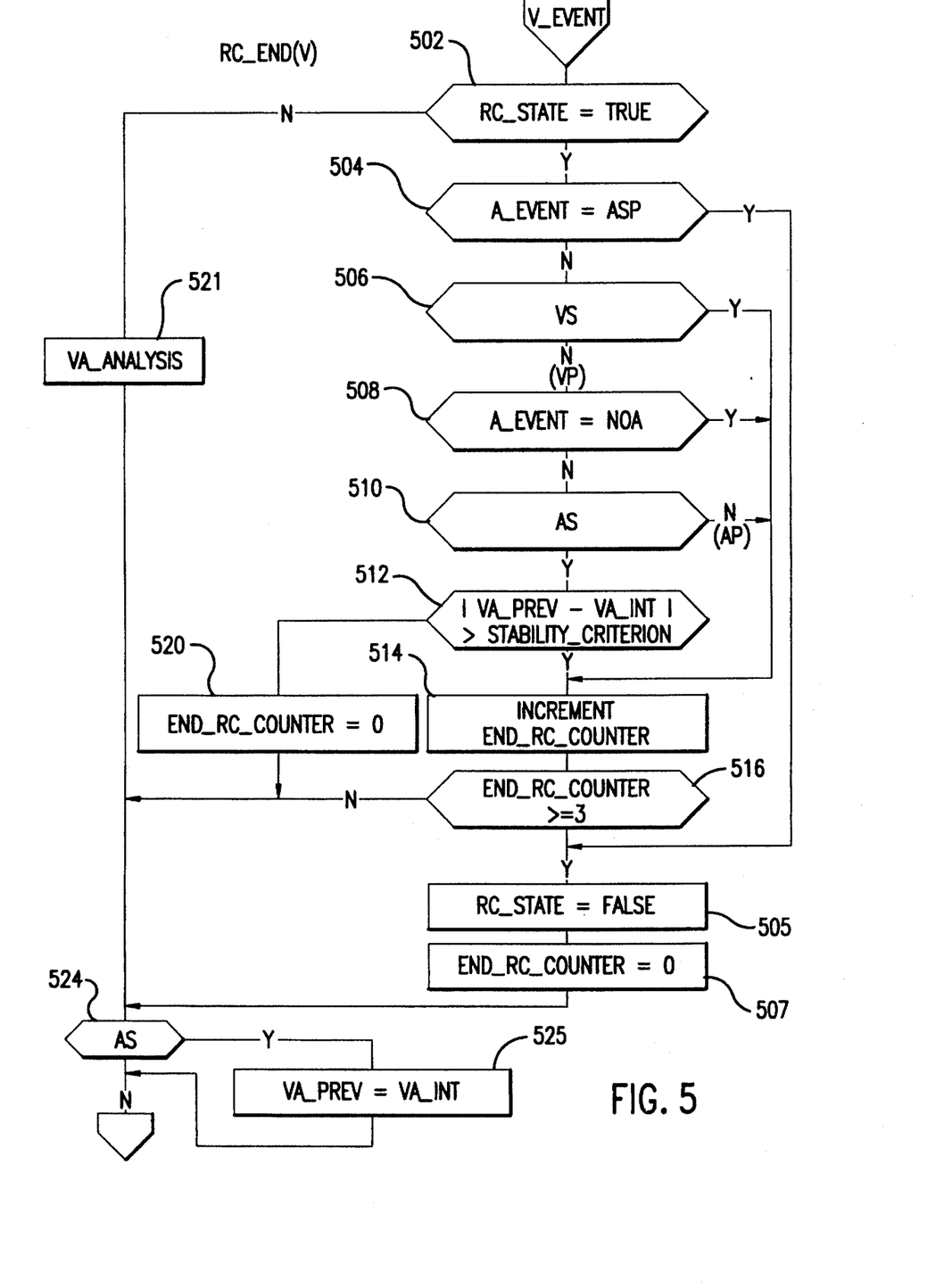
FIG. 5 is a flow diagram following a second routine End_RC(V) for determining End_RC, carried out following a ventricular event.

The event may be a V-sense, in which case the pacemaker goes to block 340 and handles the response to a V-sense; see referenced application Ser. No. 08/329,232. Or, there can be timeout of the V_Esc, as when the pacemaker is tracking or in the asynchronous mode. In this case the pacemaker goes to block 342 for V_Pace_Handling, i.e., delivers the V-stimulus and records that the V_event was a ventricular pulse (VP). Following either block 340 or 342, the pacemaker goes to 343 and carries out the RC_End (V) routine, which is illustrated in FIG. 5. Note that detection of RC, which is also done in this path, is not shown; when the pacemaker is not in RC mode, the detect RC operation is also performed at 343. See referenced U.S. Pat. No. 5,247, 929.

Figure 4:
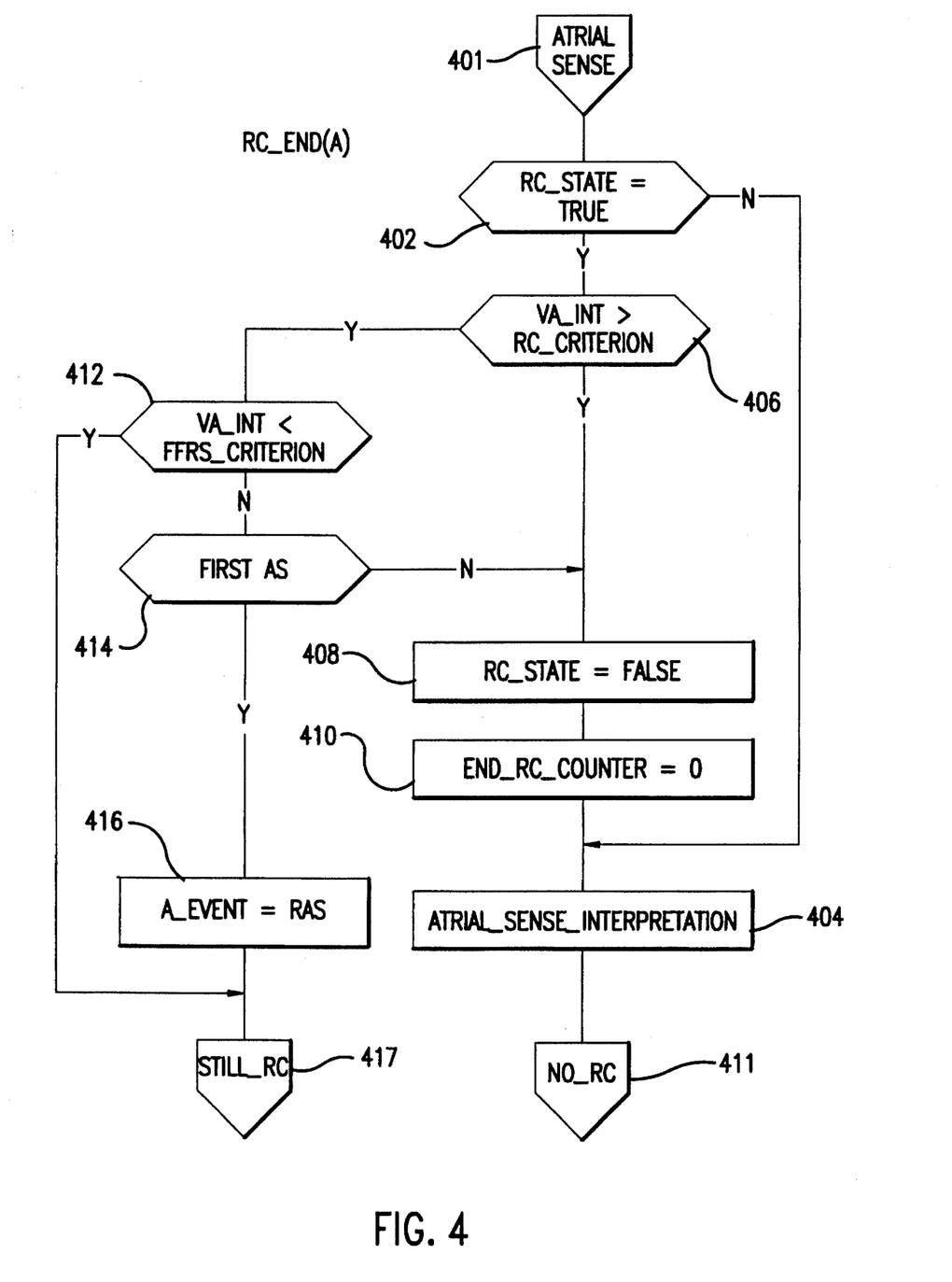
FIG. 4 is a flow diagram showing a first routine End_RC(A) for determining End_RC, carried out following an atrial sense.

Referring now to FIG. 4, there is shown a flow diagram of the End_RC (A) routine, being a series of steps taken by the pacemaker after each atrial sense. After the atrial sense at 401, at 402 it is determined whether the pacemaker is already in the RC mode, i.e., is RC_State TRUE! If no, the routine skips to block 404, and carries out the atrial sense interpretation steps. It then exits at 411, on the "No RC" path (see FIG. 3B). However, if yes, this means that the pacemaker is in an RC mode, and accordingly it will look to determine whether RC has ended. At 406, the VA interval is compared to the time within which a retrograde conduction is expected, designated the RC criterion, e.g., 450 ms. If VA interval is greater than RC criterion, this indicates that the last A sense was not retrograde, and the routine branches directly to block 408 and sets RC state to FALSE. Following this the RC counter is set equal to zero at 410, and the routine continues on to atrial sense interpretation. The function of the RC counter is discussed in connection with FIG. 5.

Returning to block 406, if the VA interval is not greater than the RC criterion, the routine branches to 412, and determines whether that interval is less than the FFRS criterion, e.g., about 150 ms. Below the FFRS, an atrial sense would in all probability be a far field R wave sense. If yes, this means that the atrial sense was not retrograde. Such an FFRS is not in fact a real atrial contraction, and the pacemaker must wait to examine further atrial senses to decide whether RC continues or is ended. Accordingly, if the answer is yes at 412, the routine branches to "Still_RC" at 417. But if no, meaning that VA interval is within the RC range, e.g., about 150–450 ms, the routine goes to 414 and determines whether this is the first AS detected in the current cycle. Note that a signal identified at 412 as an FFRS is not counted as a prior AS. If yes, the routine goes to 416 and identifies the A event as an RAS. However, if it is not the first AS, the routine branches to 408 and sets the RC state to false. Thus, following any cycle with an atrial sense, the pacemaker immediately thereafter will go out of RC mode if the VA interval is outside of the predetermined RC range, or if there has been more atrial senses within the current cycle (not including far field R wave senses).

Referring now to FIG. 5, there is shown a flow diagram of an End_RC (V) routine, which is carried out each ventricular cycle, following a ventricular event. The purpose of this routine is to immediately restore the pacemaker to a normal tracking state following delivery of an atrial sync pulse, or following a determination of three of a plurality of consecutive special events. Since the ASP is delivered after an atrial sense, AV synchrony must be restored, provided that the atrium is not refractory when the ASP is delivered. This is ensured by requiring that the AA interval between the atrial sense and the ASP, is greater than a predetermined minimum. Additionally, there are a number of other "special" events which do not immediately indicate that RC state should be terminated immediately, but suggest that RC has ended when they occur in a pattern. Accordingly, in the preferred embodiment, the occurrence of three consecutive cycles characterized by one of such special events is determined to indicate the end of retrograde conduction. These special events may be the following, depending upon the implemented algorithm:

VS: A single VS is not sufficient to indicate the end of RC, since this event could in reality be a ventricular extrasystole (VES) occurring within the AV delay. However consecutive VS events do indicate an end of RC.

VES: VES could possibly be the result of atrial undersensing. But if it is truly a VES, it could support RC and should therefore not be counted. The decision as to whether to identify VES as a special event must be based on the probability of undersensing, which is higher for a VDD pacemaker than a DDD pacemaker.

AP: Atrial pacing presumes lack of retrograde conduction. However, in a pacemaker operating with a flywheel feature, atrial pacing does not necessarily lead to ending RC. The decision as to whether or not to count AP is based on timing aspects of the implemented flywheel algorithm.

NOA: A single NOA (no atrial event) could be the result of undersensing; several NOAs are probably the result of blanking atrial events by the blanking hardware, due to the VP. The timing of the events would indicate when the atrial event was not an RAS.

VA STABILITY: When RC exists, the VA interval tends to be very stable, i.e., there is little variation from cycle to cycle. Consequently, when VA_int is unstable, or exhibits variation from cycle to cycle, RC has probably ended. A test can be made by comparing VA_int with the previous value, i.e., (VA_Prev-VA_int)>stability criterion. This test thus concerns spontaneous variations in VA interval, and is not the result of any modulation.

Referring now to FIG. 5, there is shown a flow diagram executed after the ventricular event, which incorporates the above observations. For purposes of illustration, each of VS, NOA, AS and instability is deemed to be a special event; VS could also be VES. Starting at 502, if RC state is not TRUE, meaning that the pacemaker is not in the RC mode, the routine simply branches to 521, where it does a VA analysis in support of a start of RC test. At 524, it is determined whether there has been an AS. If yes, the variable VA_Prev is set equal to the VA_int of this cycle, and the routine exits. Returning to 502, if the pacemaker is in the RC mode, the routine continues to 504. If the A event has been an ASP, the routine branches directly to block 505, sets the RC state to false, and then at 507 resets the RC counter to zero. If the A event has not been an ASP, the routine goes to block 506, and determines whether there has been a VS. If yes, the routine treats it as a special event, and branches to block 514. If there has been no VS, i.e., there has been a VP, the routine goes to 508 and determines whether there has been no atrial event during the previous ventricular interval, indicated by NOA. Again, if yes, the routine treats it as a special event and branches to block 514. If no, the routine goes to 510 and determines whether there has been an AS. If no, meaning there has been an AP, it is treated as a special event and the routine branches to 514. If at 510 it is determined that the atrial event was an AS, the routine goes to 512 and carries out the stability test, comparing the magnitude of VA_Prev-VA_int to a predetermined stability criterion, e.g., 10–20 ms. If the difference exceeds the stability criterion, this is treated as a special event, and the routine goes to block 514. At 514, the End_RC counter is incremented, and then at 516 the counter is examined to see whether it is equal to or greater than a fixed number, e.g. 3. If yes, this indicates an end of RC, and the routine goes to block 505. If no, indicating that RC end has not yet been determined, the routine branches to block 524.

Returning to block 512, if there is no instability detected, this means that there has been no special event this cycle; since there has been an AS followed by a VP, there is a good probability that retrograde conduction continues. The routine goes to 520 and resets the End_RC counter to zero.

The End_RC counter illustrated in FIG. 5 is cleared (at block 507) as soon as End_RC is determined. This is done in order to start with an empty counter at the beginning of RC. For this reason, it is likewise necessary to clear the End_RC counter following the atrial event, as seen at block 410 in FIG. 4. Further, in order to prevent a false determination of End_RC, the End_RC counter should be reset when there is a cycle with other than a special event.

It is thus seen that there is provided a system and method for determining the end of RC, and enabling the pacemaker to switch immediately from asynchronous operation back to synchronous or a tracking mode of operation. The approach of this invention focuses on continuous monitoring of events, after any atrial sense and after each ventricular event, as long as the RC state is maintained. This invention avoids a delayed return to tracking operation, which can be highly symptomatic and even be conductive to re-establish the retrograde conduction. The pacemaker of this invention waits until the end of RC actually occurs, and then immediately senses the characteristics that indicate such, enabling a direct return to synchronous operation.

What is claimed is:

1. A dual chamber pacemaker having atrial sense means for sensing signals in the atrium, ventricular pace means for generating ventricular pace pulses for delivery to a patient's ventricle, sync means for controlling said ventricular pace means to deliver said pace pulses in synchronized relation to sensed atrial signals, and RC means for determining the occurrence of retrograde conduction and for placing said pacemaker in an RC mode when retrograde conduction is determined, and RC end means operative each pacemaker cycle while in said RC mode for determining when retrograde conduction is stopped and for taking said pacemaker out of said RC mode, said RC end means comprising:

VA timing means for determining the VA interval between a ventricular pace pulse and a sensed atrial signal, compare means for comparing said VA interval against predetermined RC timing criteria and for determining end of RC as a predetermined function of said comparison, ventricular detect means for detecting when at least one predetermined event occurs during a cycle and for determining when a pattern of such predetermined events has been found, and mode switch means for taking said pacemaker out of said RC mode immediately when either end of RC is determined by said RC end means or said pattern of events has been found.

2. The pacemaker as described in claim 1, wherein said ventricular detect means comprises means for determining when the last VA interval is different from the preceding VA interval by at least a predetermined amount.

3. The pacemaker as described in claim 1, further comprising ASP means for delivering an atrial sync pulse while said pacemaker is in said RC mode and when predetermined ASP criteria are met, and wherein said mode switch means takes said pacemaker out of said RC mode whenever an atrial sync pulse has been delivered.

4. The pacemaker as described in claim 1, wherein said RC end means further comprises means for determining when there have been two atrial senses without an intervening ventricular event, and said mode switch means takes said pacemaker out of said RC mode when a said second atrial sense has been determined.

5. The pacemaker as described in claim 1, wherein said ventricular detect means comprises means for determining the occurrence of any one of a plurality of predetermined events, and for determining a said pattern when three successive such events are recognized.

6. The pacemaker as described in claim 1, wherein said VA timing means is operative after each atrial sense.

7. The pacemaker as described in claim 1, wherein said ventricular detect means is operative after each ventricular event.

8. The pacemaker as described in claim 1, comprising means for comparing the VA interval of a cycle with the VA interval of a prior cycle, and for determining a predetermined event when said comparison indicates instability.

9. The pacemaker as described in claim 1, wherein said ventricular detect means detects predetermined events from a class of events including VS, NOA, and AS.

10. The pacemaker as described in claim 9, wherein said class of events includes the event of VA instability.

11. A dual chamber pacemaker having atrial sense means for sensing signals in the atrium, ventricular pace means for generating ventricular pace pulses for delivery to a patient's ventricle, VA_interval means for determining the interval from a delivered ventricular pace pulse to a sensed atrial signal, sync means for controlling said ventricular pace means to deliver said pace pulses in synchronized relation to sensed atrial signals, and RC means for determining the occurrence of retrograde conduction and for placing said pacemaker in an RC mode when retrograde conduction is determined, and RC end means operative each pacemaker cycle while in said RC mode for determining when retrograde conduction is stopped and for taking said pacemaker out of said RC mode, said RC end means comprising VA instability means for determining when a said VA interval is different from at least the VA interval of the prior cycle by a predetermined amount indicating instability, means for determining when there have been two atrial senses without an intervening ventricular event and mode switch means for taking said pacemaker out of said RC mode when either said instability is detected or said two atrial senses are detected.

12. The pacemaker as described in claim 11, comprising comparing means for comparing a said VA interval against a predetermined RC range.

13. The pacemaker as described in claim 12, wherein said RC range is about 150–450 ms.

14. A dual chamber pacemaker system having atrial sense means for sensing atrial signals from the patient's atrium, ventricular pace means for generating ventricular pace pulses for delivery to a patient's ventricle, VA interval means for determining the interval from a ventricular pace pulse to a sensed atrial signal, control means for normally controlling said ventricular pace means to deliver said pace pulses in synchronized relation to sensed atrial signals, RC means for determining the occurrence of retrograde conduction and for placing said pacemaker in an RC mode when retrograde conduction is determined, further comprising:

(a) first means operative after each atrial sense for comparing the timing of the VA interval against predetermined criteria, (b) second means operative after each ventricular event for determining the occurrence of a predetermined pattern of events and (c) RC_End means for ending said RC mode as a function of said first and second determinations.

15. A method of controlling the mode of operation of a dual chamber pacemaker, said pacemaker having atrial sense means for sensing signals from a patient's atrium, ventricular pace means for generating ventricular pace pulses for delivery to said patient's ventricular, and control means for controlling the timing of said ventricular pace pulse generated by said ventricular pace means, said method comprising the following steps:

determining the occurrence of retrograde conduction and placing said pacemaker in an RC asynchronous mode of operation when retrograde conduction is determined;

determining VA instability following each sense of an atrial signal while said pacemaker is in said RC mode, and immediately switching said pacemaker into a synchronous mode upon a determination of VA instability; and detecting, when said pacemaker is in said RC mode, the occurrence of one of a predetermined class of special events, determining a predetermined pattern of said detected special events over n cycles, and switching said pacemaker out of said RC mode and into a synchronous mode upon a determination of a said pattern.

* * * * *